US006531321B1

(12) United States Patent
Ryan et al.

(10) Patent No.: US 6,531,321 B1
(45) Date of Patent: Mar. 11, 2003

(54) BLOOD CONTROL AND SYSTEM FOR ERYTHROCYTE SEDIMENTATION MEASUREMENT

(75) Inventors: Wayne L. Ryan, Omaha, NE (US); Bradford A. Hunsley, LaVista, NE (US)

(73) Assignee: Streck Laboratories, Inc., La Vista, NE (US)

( * ) Notice: Subject to any disclaimer, the term of this patent is extended or adjusted under 35 U.S.C. 154(b) by 246 days.

(21) Appl. No.: 09/662,960

(22) Filed: Sep. 15, 2000

(51) Int. Cl.$^7$ .............................................. G01N 33/86

(52) U.S. Cl. .............................. 436/70; 436/8; 436/10; 436/16; 252/408.1; 600/370; 73/61.65

(58) Field of Search ................................. 436/8, 10, 11, 436/16, 18, 68, 70; 435/2; 252/408.1; 600/370; 73/61.65

(56) References Cited

U.S. PATENT DOCUMENTS

| | | | |
|---|---|---|---|
| 2,102,785 A | | 12/1937 | Brooks |
| 2,727,383 A | | 12/1955 | Dalter |
| 2,848,368 A | | 8/1958 | Witt |
| 2,929,764 A | | 3/1960 | Hultin et al. |
| 3,660,037 A | | 5/1972 | Sokol |
| 3,873,467 A | | 3/1975 | Hunt |
| 4,064,118 A | | 12/1977 | Wong |
| 4,102,810 A | | 7/1978 | Armstrong |
| 4,264,470 A | | 4/1981 | Chastain, Jr. et al. |
| 4,299,726 A | | 11/1981 | Crews et al. |
| 4,324,686 A | | 4/1982 | Mundschenk |
| 4,358,394 A | | 11/1982 | Crew et al. |
| 4,436,821 A | | 3/1984 | Ryan |
| 4,489,162 A | | 12/1984 | Hawkins et al. |
| 4,572,899 A | | 2/1986 | Walker et al. |
| 4,704,364 A | | 11/1987 | Carver et al. |
| 4,777,139 A | | 10/1988 | Wong et al. |
| 5,316,729 A | | 5/1994 | Orth et al. |
| 5,328,822 A | | 7/1994 | McKinney |
| 5,380,664 A | | 1/1995 | Carver et al. |
| 5,482,829 A | | 1/1996 | Kass et al. |
| 5,529,933 A | | 6/1996 | Young et al. |
| 5,622,806 A | * | 4/1997 | Veregin et al. .......... 430/108.6 |
| 5,863,799 A | | 1/1999 | Hengstenberg |
| 5,888,822 A | | 3/1999 | Hengstenberg |
| 5,895,760 A | | 4/1999 | Chen et al. |
| 6,017,764 A | | 1/2000 | Chen et al. |
| 6,051,433 A | | 4/2000 | Hengstenberg |
| 6,124,089 A | | 9/2000 | Ryan |
| 6,159,682 A | * | 12/2000 | Ryan .......................... 435/39 |
| 6,200,500 B1 | * | 3/2001 | Ryan ....................... 252/408.1 |
| 6,221,668 B1 | * | 4/2001 | Ryan et al. ............... 252/408.1 |
| 6,265,148 B1 | * | 7/2001 | Ryan ....................... 435/283.1 |
| 6,331,435 B1 | * | 12/2001 | Hengstenberg .............. 436/10 |
| 6,342,391 B1 | * | 1/2002 | Chen et al. ............... 252/408.1 |
| 6,399,388 B1 | * | 6/2002 | Ryan et al. ............... 252/408.1 |
| 6,403,377 B1 | * | 6/2002 | Ryan et al. ............... 252/408.1 |
| 6,406,915 B2 | * | 6/2002 | Ryan et al. ............... 252/408.1 |

FOREIGN PATENT DOCUMENTS

WO  US96/15628  4/1997

OTHER PUBLICATIONS

Thomas, Et. Al, "Calibration and Validation for Erythrocyte Sedimentation Tests," Arch. Pathol. Lab, vol. 117, pp. 719–723, (Jul., 1993).
Excerpt from Sedimatic User Manual & Technical Reference by Analysis Instrument, Date Unknown.
Equinox–SED Rate product information, Date Unknown.
ESR CHEX and ESR 8 Product Information, Date Unknown.
Identification of commonly owned co–pending application (see Information Disclosure Statement).
Bull Et. Al, "The Zeta Sedimentation Ration," Blood, vol. 4 (No. 4), p. 550, (Oct. 1972).
De Castro Et. Al, "Valoracion de un sistema alternativo totalmente automatizado para la determinacion de law velocidad de sedimentacion globular," Sangre, vol. 34 (No. 1), pp. 4–9, (1989).
International Committee for Standarization in Haematology (ICSH), Recommendation for Measurement of Erythrocyte Sedimentation Rate of Human Blood, Am. J. Clin. Patho. 68: 505–512 (1981).
International Committee for Standarization in Haematology (ICSH), Reference Method for the Erythrocyte Sedimentation Rate (ESR) Test on Human Blood, Br. J. Haematol. 24:671 (1972).
Jou Et. Al, "Evalucion de un sistema totalmente automatico para realizar la velocidad de sedimentacion globular," Sangre, vol. 33, pp. 474–478, (1988).
Product Brochure, Dispette, Ulster Scientific, Inc., New Paltz, NY, date unknown,.
Product Brochure, Dispette 2, Ulser Scientific, Inc., New Paltz, date unknown.
Todd–Sanford Clinical Diagnosis by Laboratory Method (15th edition), Erythrocyte Sedentimation Rate (ESR, edited by Davidsohn, I., and Henry, Jr. pp. 133–135, WB Sauders Company, London, Toronto (1974).
Landaas Et Al., "The Quality of Laboratory Analyses in the Primary Health Care," Scan J. Prim Health Care, vol. 4, pp. 169–173, (1986).
JP 01199158 Seitetsu Chem Ind. Co., Ltd. (Jananese Abstract).
Harkness, J., "A New Instument for the Measurement of Plasma Visosity," Lancet, p. 280–281, (1963).
Fahraeus, Robin, "Acta Medica Scandinavica," pp. 1–228, (1921) and excerpt (p. 121).

(List continued on next page.)

Primary Examiner—Maureen M. Wallenhorst
(74) Attorney, Agent, or Firm—Dobrusin & Thennisch PC

(57) ABSTRACT

A control and system for blood testing, including a control having stabilized blood cells that have been introduced into a suspension including an aggregating agent and preferably a surfactant. The control and system is used advantageously for indirect acute protein plasma measurement, including erythrocyte sedimentation rate testing.

28 Claims, No Drawings

OTHER PUBLICATIONS

Westergren, A., "Studies of the Suspension Stability of the Blood in Pulmonary Tuberculosis," Acta Medica Scandinavica, pp. 247–282, (1921).

Kushner, I., "The Phenomenon of the Acute Phase Response," Ann N.Y. Acad. Sci, p. 39–48 (1982).

Gabay, Cem Et. Al, "Acute–Phase Proteins and Other Systemic Responses to Inflammation," The New England Journal of Medicine, pp. 448–454, Feb. 1990.

Moshage, Han, "Cytokines and the Hepatic Acute Phase Response," Journal of Pathology, vol. 181, pp. 257–266, (1997).

Cooke, B.M. Et. Al, "Automated Measurement of Plasma Viscosity by Capillary Viscomenter. J. Clin. Pathol," vol. 41, pp. 1213–1216, (1988).

Stuart, J., Kenny, "Blood Rheolgy.J. Chin. Path," vol. 33, pp. 417–429, (1980).

"Guidelines on Selection of Laboratory Test for Monitoring the Acute Phase Response. J. Clin Pathol." vol. 41, pp. 1203–1212, (1988).

The Clinical Laboratory Improvement Act (CLIA–88), 42 C.F.R., Part 493, Subpart K (12), 1999.

Fujil, T., "Shape Changes of Human Erythrocytes Induced by Various Amphiphathic Drugs Acting on the Membrane of the Intact Cells," Biochem J. Pharmacology, vol. 28, pp. 613–620, (1979).

Hema–Trol/Sedratrol Product Information, 1999.

Gregersen, M. Et. Al, "Relation of Molecular Size of Dextran to its Effect on the Rheological Properties of Blood (28198)," Proceedings of Society for Experimental Biology & Medicine, pp. 883–886, 1963.

Strauss, R., "In vitro Comparison of the Erythrocyte Sedimenting Properties of Dextran, Hydroxyethyl Starch and New Low–Molecular–Weight Hydroxyethyl Starch, Vox Sang," vol. 37, pp. 268–271, (1979).

Meiselman, H., "The Influence of Dextran on the Sedimentation Behavior of Human Red Cell: Macro and Micro Studies. 5th Europ. Conf. Microcirculation," Gothenburg 1968. Bibl. Anat, pp. 20–31, (1968).

* cited by examiner

BLOOD CONTROL AND SYSTEM FOR ERYTHROCYTE SEDIMENTATION MEASUREMENT

BACKGROUND OF THE INVENTION

1. Technical Field of the Invention

The present invention relates to blood controls and more particularly to controls for use in indirect acute phase protein measurement tests.

2. Background

There are various methods that have been described which result in the indirect measurement of the acute-phase (inflammatory response) proteins, including the erythrocyte sedimentation rate (ESR) test, the Zeta Sedimentation Ratio Test, and Plasma Viscosity Test. See Bull, B., Brailsford, D. The Zeta Sedimentation Ratio. Blood. 1972; 40: 550–559. Harkness, J. A New Instrument for the Measurement of Plasma Viscosity. Lancet. 1963; 280–281.

By way of the history, possibly the first detailed method for indirectly measuring (by erythrocyte sedimentation) acute-phase proteins was described by Fahraeus in 1921. Fahraeus, Robin. Acta Medica Scandinavica. 1921; 55:1–228. The test was later modified by Fahraeus and Westergren. Westergren, A. Studies of the Suspension Stability of the Blood in Pulmonary Tuberculosis. Acta Medica Scandinavica. 1921;54:247–282. Although there have been many modifications of this manual test, the basic method has survived. The method involves diluting blood, filling a standardized tube, and measuring the distance the red cells settle in a specific time interval.

The erythrocyte sedimentation rate test (ESR) measures the proteins of blood that are increased by inflammation. The presence of these proteins causes an increase in viscosity and also causes the red cells to sediment more rapidly. The mechanisms for the changes in these proteins are better understood today than when the test was introduced by Fahraeus in 1921. Fahraeus, Robin. Acta Medica Scandinavica. 1921; 55: 1–228 (page 121). However, he recognized the importance of fibrinogen and globulins which are the major proteins producing an increased ESR.

It is believed that the basis for the increased sedimentation is due to a group of proteins called acute phase proteins. These are macromolecules of the plasma such as fibrinogen and the globulins. The proteins are synthesized in the liver and their levels in the plasma rise with inflammation. Kushner, I. The Phenomenon of the Acute Phase Response. Ann N.Y. Acad. Sci. 1982; 389: 39–48. Han Moshage divides the acute phase proteins into two groups: (1) Tvpe I proteins, which include serum amyloid, C-reactive protein, Complement C3, haptoglobin and $\alpha$1-acid glycoprotein. Io These are induced by interleukin- 1-like cytokines such as IL-1$\alpha$, IL-1B, TNF-$\alpha$, and TNF-B; and (2) Type II proteins, which are induced by IL-6 like cytokines which include IL-61, LIEF, IL-II, OSM, CNTF, and CT-1. The IL-6 will synergize with IL-1 to induce the Type I proteins of the cytokines. IL-6 is believed to be the main cause of the induction of acute-phase proteins. Gabay, Cem et al. Acute-Phase Proteins and Other Systemic Responses to Inflammation. The New England Journal of Medicine. 448–454. Moshage, Han. Cytokines and the Hepatic Acute Phase Response. Journal of Pathology. 1997; 181:257–266.

Coulter Corporation has offered an instrument, the ZETAFUGE, for determining the zeta sedimentation ratio. Bull and Brailsford (Bull, B., Brailsford, D. The Zeta Sedimentation Ratio. Blood 1972; 40; 550–559) have described a method for making controls or "standards" for this system.

The plasma viscosity test is commonly employed for indirectly measuring acute phase proteins in the United Kingdom. One suitable instrument, the Viscometer, and controls for it are manufactured by Coulter Corporation. This technique was described by Cooke and Stuart in 1988. An earlier article describing this methodology was published in the J. Clinical Pathology in 1980 by Stuart and Kenny. Cooke, B. M. et al. Automated Measurement of Plasma Viscosity by Capillary Viscomenter. J. Clin Pathol. 1988; 41:1213–1216. Stuart, J., Kenny, M. W. Blood Rheology. J. Clin Path. 1980; 33:417–429.

Other automated instruments have appeared on the market. Examples include the Ves-Matic®, Mini-Ves®, Sed-Mat®, and ESR-8/Sedimatic 8™.

Methods for determining acute phase proteins can be influenced by numerous factors. Several of these relate to the type of tube used and other environmental conditions. For instance, bench-top vibration, temperature and tube angle may affect rates obtained. The need for using control preparations for these methods is well established. The ICSH Committee has addressed this issue in 1988 (International Committee for Standardization in Haematoloy (Expert panel on Blood Rheology). Guidelines on Selection of Laboratory Tests for Monitoring the Acute Phase Response. J. Clin Pathol. 1988; 41; 1203–1212) and 1993 (Thomas, Robert et al. Calibration and Validation for Erythrocyte Sedimentation Tests. Arch Pathol Lab Med. 1993; 117; 719–723). They describe the use of selected blood specimens for quality controlling the "routine" ESR method by comparison to the "reference" method. One control for use in a particular ESR test is that addressed in U.S. Pat. Nos. 5,863,799 and 5,888,822. The Clinical Laboratory Improvement Act (CLIA-88) mandated that control preparations be used for all automated instruments. See, e.g., 42 C.F.R., Part 493, Subpart K (12), incorporated by reference herein. Prior to CLIA-88, the use of controls was not mandated.

As to the effect of aliphatic alcohol on blood, reference should be made to Mol Biol (Mosk) 1992 Mar-Apr;26(2):315–20 (English Abstract).

From the above it is clear that the concept of using control preparations for monitoring all three methods has been well known. Unmodified human blood can provide controls which have limited stability. In those instances, the controls are used in applications where the stability that is desired is less than several months.

SUMMARY OF THE INVENTION

One preferred method for achieving long-term stability in a control includes the combination of using a diluent having red blood cells suspended therein along with an aggregating agent and preferably a surfactant. In one embodiment, the cells are fixed morphologically, such as with a suitable aldehyde (e.g., glutaraldehyde). In a particularly preferred embodiment, the aggregating agent has cationic characteristics. Controls made according to the present invention are useful for acute phase protein measurement in systems using a manual, semiautomated or automated test apparatus. The controls are stable over long-term and short-term intervals.

Preparation of a long-term stable (i.e., capable of achieving up to several months of stability or shelf-life) control desirably avoids reliance on the use of unmodified fibrinogen and normal RBC. Desirably such control should exhibit long term color stability and good resuspension characteristics. Accordingly, the present control and system of the present invention provides an improved approach to indirect acute phase protein measurement. They afford the ability to have stable controls with relatively long shelf-lives, and with relative ease of manufacture. Additionally, the controls of the present invention exhibit improved long-term resistance to color change and cell clumping.

DETAILED DESCRIPTION OF THE PREFERRED EMBODIMENT

The skilled artisan will appreciate that the present invention is not limited to the embodiment shown, but advantageously may be modified or adapted for the systems as disclosed in one or more of U.S. Pat. Nos. 6,159,682; 6,124,089; 6,017,764; 5,895,760; 6,051,433; 5,888,822; and 5,863,799; as well as U.S. Pat. application Ser. No. 09/303, 719 (now abandoned) accordingly each of such patents and applications is hereby expressly incorporated by reference for all necessary purposes.

To prepare a preferred control of the present invention, a predetermined amount of a simulated red blood cell is provided. The simulated red blood cell is combined with an aggregating agent, a surfactant and optionally one or more agents such as an alcohol, a disinfectant, or a mixture thereof.

In one preferred embodiment, the simulated red blood cell is prepared from an actual blood source, and the simulated red blood cell component of the control is an actual red blood cell that has been treated to preserve the settling characteristics of red blood cells over a prolonged period of time (i.e., greater than the useful life of untreated blood cells). In a particular preferred embodiment, the blood cells of the control of the present invention are stable for at least about 6 months (and more preferably about one year) at room temperature and at a temperature of about 6 degrees Celsius.

More specifically, when a blood source for providing red blood cells (RBC) is used, the starting blood is washed substantially free of plasma, platelets, and leukocytes preferably with a saline solution, such as one containing 1.5% polyethylene glycol-(20)(PEG-20K). This causes the red cells to aggregate and settle. After settling, the supernatant is removed. This is repeated multiple times (e.g., three times) to obtain washed red cells substantially free of contaminants. The starting blood may be from any suitable source and may be, for example, human, bovine or porcine blood. In an alternative embodiment, other surrogate RBCs can be used, being preparedfrom any known method. References herein to processing of red blood cells shall also encompass processing of surrogates.

The washed cells may be re-suspended in a suitable saline solution (e.g., in an equal volume of cells to solution of a phosphate buffered saline), or optionally, in another suitable diluent or buffer (e.g., a phosphate or citrate diluent as disclosed in the aforenoted incorporated patents and applications, HEPES, or another suitable buffer with a pKa between about 6 and about 7.5). Preferably, the cells are present in a range of about $3.9 \times 10^{12}/l$ (i.e. $3.9 \times 10^{12}$ cells/l) to about $4.1 \times 10^{12}/l$, and more preferably about $4.0 \times 10^{12}/l$.

A fixing agent (e.g., a suitable aldehyde, such as glutaraldehyde) is added. Preferably, when using glutaraldehyde it is added so that a final concentration (after final dilution) of about 0.08 g/l to about 0.48 g/l, and more preferably about 0.24 g/l glutaraldehyde, is attained. After a suitable period of time (e.g., about 24 hours), the cells are again washed with the diluent and suspended at a concentration of about $3.75 \times 10^{12}/l$ to about $4.25 \times 10^{12}/l$, and more preferably about $4.0 \times 10^{12}/l$.

The cells are heated, such as by placing them in bottles in a water bath at elevated temperature, (e.g., several degrees greater than room temperature, preferably greater than about 15° C. higher than room temperature, more preferably in the range of about 48 to about 51° C., and more preferably about 49 to about 50° C.). Heating is continued for a sufficient time to achieve desired stability. The heating preferably is maintained to result in the formation of stabilized cells of a predetermined shape (e.g., discs) in at least about 90% of the cells, more preferably at least about 95% of the cells, and still more preferably about 99% of the cells.

Further, the heating preferably is done for sufficient time and at sufficient temperature to denature at least a portion of the cell surface proteins. For instance, the heating step is preferably done at about 48° to about 51° C. (and more preferably about 49° to about 50° C.) for a period of 60 to about 75 minutes or more. Less heat may be used (e.g., as little as about 2° C. cooler), but it will produce a product with shorter shelf life. Moreover, at temperatures over about 51° C. the red cells may become permanently altered (thus affecting stability), as evidenced by the development of many small vesicles in the solution. Thus, temperature conditions advantageously can be varied to selectively adjust desired product shelf-life.

The fixing agent is then removed and the cells are washed (e.g., by washing with an equal volume of a suitable phosphate buffered saline solution ("PBS")). The red blood cell count is then adjusted to measure about $3.75 \times 10^{12}/l$ to about $4.25 \times 10^{12}/l$.

An example of a suitable PBS solution includes a mixture of one or more of a dibasic and monobasic sodium phosphate, and sodium chloride. Optionally the PBS solution includes a suitable biocide, e.g., a sulfur containing biocide, such as one or more isothiazolinones or a derivative thereof. The pH of the PBS solution preferably ranges from about 7.0 to about 7.6 and more preferably about 7.2 to about 7.4. The osmolarity of the PBS solution ranges from about 270 to about 310 and more preferably about 285 to about 300 mOsm. Thus, an example (without limitation) of a particularly preferred solution includes about 7.1 g/L dibasic sodium phosphate ($Na_2HPO_4$), about 2.1 g/L monobasic sodium phosphate ($NaH_2PO_4$), about 3.8 g/L sodium chloride and about 0.001% to about 0.05% (e.g., about 3.4 g/L) Proclin® 300 (which is about 2.3 parts 5-chloro-2-methyl-4-isothialzolin-3-one; about 0.70 parts 2-methyl-4-isothiazolin-3-one in a base of about 93–95 parts modified glycol and about 2–3 parts alkyl carboxylate, and is commercially available from Rohm and Haas).

Red blood cells are then settled, such as by gravity settling them, and the resulting supernatant is removed. Optionally, the density of the cells is increased in order to increase the inherent settling rate of the cells. That is, the cells are then reduced to about one half to about two thirds their original size, preferably without the removal or loss of hemoglobin. For instance, the cells are then resuspended (e.g., to a concentration of about $0.85 \times 10^{12}/l$ to about $1.15 \times 10^{12}/l$ in an aliphatic alcohol solution. Though other alcohols may be use, such as methanol or ethanol, one preferred alcohol solution includes about 40% to about 60% v/v 2-propanol in the PBS solution. The resulting suspension is then allowed to settle, such as by an overnight settling period. The treatment of cells with alcohol as described in the foregoing also enables long term color stability as compared with untreated cells. Thus, alcohol treated cells remain red for a longer period relative to untreated cells, and in a highly preferred embodiment, for at least 90 days at about 50° C., at least about 6 months at about 220° C. or both. In a particularly preferred embodiment, the color of the cells, the color of the suspension, or both will approximately match the color spectrum defined by the Pantone® Color Specifier designations 186C, 187C, 188C, 193C, 195C, 1795C, 1805C, and 1815C, and more preferably is about 186C, 187C or 188C. The alcohol treatment step may be omitted as desired, such as for certain cell sources (e.g., bovine).

The alcohol is then removed and the cells are resuspended in the PBS solution using any suitable protocol. For instance, the cells are washed a plurality of times (e.g., three times) with an equal volume of PBS solution. Thereafter, the concentration of cells is adjusted to the desired level. By way of illustration, a first level concentration may be about $1.8 \times 10^{12}/l$ to about $3 \times 10^{12}/l$ and more preferably about $2.2 \times 10^{12}/l$ to about $2.3 \times 10^{12}/l$; with a second level concentration of about $1 \times 10^{12}/l$ to about $1.8 \times 10^{12}/l$ and more preferably about $1.2 \times 10^{12}/l$ to about $1.4 \times 10^{12}/l$.

After the cells are prepared and suspended to an appropriate concentration, a suitable amount of one or more aggregating agents is introduced into the suspension. In a particularly preferred embodiment, the aggregating agent includes a finely divided solid material. Still more preferably, the finely divided solid material is selected from the group consisting of particles of a large polycationic molecule or polymer, particles of a mineral (e.g., clay minerals), or mixtures thereof. In general, the solids will be particulated to a particle size of less than about 45 microns (and more preferably a mean particle diameter of less than about 10 microns and at least about 95% of the particle diameters less than about 21 microns). More particularly, where the aggregating agent is a naturally occurring substance, it is preferably a mineral or clay. In a more preferred embodiment the agent preferably contains a form of silicon such as a silica, silicate or otherwise. In one embodiment, the agent is a multilayer crystalline material.

Examples of preferred aggregating agents include, but are not limited to, cationic charged particles. In a preferred embodiment, the aggregating agents are selected from diatomaceous earth (diatomaceous silica), montmorillonite or bentonite (such as that available under the trade designation COLLOID BP, form Southern Clay Products), polyethylenimine (e.g., such as that available from BASF under the designation LUPASOL P or PS), or mixtures thereof. One preferred polyethylenimine has a weight average molecular weight of about 700,000 to about 1,000,000, a pH of about 10 to about 12, or both. Of course, other equivalent agents may also be employed. Examples of alternative suitable commercial materials include COLLOID MO, BENTOLITE H, GELWHITE GP, or the like.

Depending upon the aggregating agent employed, the amount of the aggregating agent employed in the suspension ranges from about 0.001 to about 2% or larger (about 1 mg % to about 200 mg %), and more preferably about 0.0025 to about 0.05% (about 2.5 mg % to about 50 mg %). Other concentrations may also be employed.

In one preferred embodiment, a surfactant is also admixed into the suspension. The surfactant may be any suitable surfactant, and may be anionic, cationic, amphoteric or nonionic. In general the preferred surfactant has an alkylene oxide group, and preferably an ethylene oxide group. Such group may be part of a block copolymer, fluorinated, or in a waxy state. An example of one (but certainly not the only one) suitable commercially available surfactant is sold under the trade designation Triton X-705 (Union Carbide). The concentration of the surfactant employed preferably ranges from about 0.01 to about 2% and more preferably about 0.025 to about 0.050% (about 25 mg % to about 50 mg %) of the suspension. Examples of other suitable commercially available surfactants include PLURONIC F-88 (BASF), PLURONIC F-86 (BASF), PEG 1450, ZONYL FSN (DuPont), ZONYL FSJ (DuPont) or the like.

It will be appreciated that the amount of surfactant, aggregating agent or both employed may vary depending upon the level of concentration of cells. By way of example, if a first level concentration of red blood cells is about $2.25 \times 10^{12}/l$, the amount of surfactant (Triton X-705 (10% stock in PBS)) is about 50 mg %, as compared with about 25 mg % for a second level red blood cell concentration of about $1.3 \times 10^{12}/l$. For illustration purposes, in these examples, the aggregating agent is either Lupasol P (1% stock in PBS), employed at about 5 mg % for the first level concentration and about 2.5 mg % for the second concentration level. Alternatively, the aggregating agent is Colloid BP (2.5% stock in PBS) at about 50 mg % for the first level and about 25 mg % for the second level.

In an alternative embodiment one or more additional or alternative aggregating agents may be suitably employed in accordance with art disclosed teachings, including but not limited to methylcellulose, polyvinylpyrolidine, dextran or any of the aggregating agents disclosed in the aforenoted incorporated patents and applications.

An alternative method to obtain generally uniform cell shape is also used when the RBC do not initially have a disc shape. If they are significantly crenated, they may be first treated (e.g., by treating the cells with a suitable drug) to induce shape changes in the RBC membrane. After addition of the drug, the cells are fixed (e.g., with glutaraldehyde at about 0.24 g/l and then heated to about 48°–50° C. Examples of drugs which may be used are amphipathic drugs, such as phenothiazine drugs, and particularly chlorpromazine, promethazine or a combination. See Fujil, T. Shape Changes of Human Erythrocytes Induced by Various Amphipathic Drugs Acting on the Membrane of the Intact Cells. Biochem J. Pharmacology. 1979;28:613–620. When added to red cells at concentrations of 0.001% –0.01% w/v, the shape change ordinarily occurs within a few minutes. Then the cells may be processed according to known techniques to obtain substantially uniform shapes.

It should be appreciated that other additives may be incorporated into the final control to obtain desired characteristics. Likewise, as seen from the Example and elsewhere herein, various additives may be used to help prepare the blood cells.

The systems of the present invention contemplate the use of a control of the present invention with erythrocyte sedimentation measurement instruments, including manual, semiautomated and automated instruments. Examples include the classical Westergren, Modified Westergren, Wintrobe, ESR-8 (available through Streck Laboratories (Omaha, Nebr.)), Ves-Matic®, and Mini-Ves®. When used, the system of the present invention satisfies CLIA-88 requirements.

Controls may be provided at different sedimentation levels (e.g., less than 20 mm/hr and greater than 30 mm/hr or as otherwise desired). Controls may be supplied as part of a kit for use with the instruments. For instance, a plurality of suitable vials or reservoirs having a predetermnining volume (e.g., about 9 ml), preferably having pierceable cap, may be provided. Any suitable rack having leveling indicators and adjustability may be used to hold the vials. The preferred control of the present invention advantageously exhibits 95-day closed vial (and more preferably one year), 31-day open-vial stability or both.

Controls prepared in accordance with the present invention exhibit enhanced resuspension characteristics as compare with previous controls. For instance, as compared with a control employing methyl cellulose in its art disclosed amounts as the aggregating agent, the controls of the present invention are capable of exhibiting at least a two-fold, more preferably four-fold and still more preferably eight-fold increase in the rate of resuspension (which is deemed complete when visual inspection reveals no apparent red blood cells in their starting location, such as at the bottom of a vial). In a particularly preferred embodiment, such results are exhibited after being stored upright at about 18–22° C. for at least 60 days, and where the test vials oriented with its longitudinal axis generally horizontally are mixed on a multipurpose rotator at a minimum speed of about 30 rpm. Resuspension is also achievable in the controls of the present invention using less advance mixing of the test samples as compared with prior art controls.

In more fully automated systems, the system includes a suitable computer for receiving, storing, or transmitting data about specimen(s) tested. Bar code reader devices can be used to identify specimens and transmit information. Printers and other peripheral devices can be incorporated into the system to help manage data.

The following examples are provided by way of illustration and are not intended as limiting.

EXAMPLE 1

The following procedure outline is performed:

1) Fix and stabilize human RBC with 0.08% glutaraldehyde, with the glutaraldehyde calculation being based on volume, RBC count ($4.0\times10^{12}/l\pm0.25\times103^{2}/l$) and target glutaraldehyde concentration.
2) Remove the glutaraldehyde by washing glutaraldehyde treated RBC three times with an equal volume of PBS. Adjust the RBC count to $4.0\times10^{12}/l\pm0.25\times10^{12}/l$ after completion of the washing segment.
3) Gravity settle the RBCs and remove the resulting supernatant. Resuspend the RBC with a solution of 40% 2-Propanol in PBS (v/v), and to a count of $1.0\times10^{12}/l\pm0.15\times10^{12}/l$. Gravity settle the alcohol treated RBCs overnight.
4) Remove alcohol solution and resuspend the RBCs in PBS. Wash RBCs 3 times with an equal volume of PBS. Following completion of the washing segment, adjust the RBC counts according to the level specific specifications. The RBC specification for level #1 is set at $2.25\times10^{12}/l\pm0.05\times10^{12}/l$. The RBC specification for level #2 is set at $1.3\times10^{12}/l\pm0.05\times103^{12}/l$.
5) Add Colloid BP (2.5% stock solution in PBS) to the RBC pool volumes according to the level specific specifications, so that the final Colloid BP concentration for level #1 is at 50 mg % (20 ml of Colloid BP stock/liter of product) and 25 mg % for level #2 (10 ml of Colloid BP stock/liter of product). Mix thoroughly.
6) Add Triton X-705 (10% stock solution in PBS) to the RBC pool volumes according to the level specific specifications, so the Final Triton x-705 concentration for level #1 is at 50 mg % (5.0 ml of Triton X-705 stock/liter of product) and 25 mg % for level #2 (2.5 ml of Triton X-705 stock/liter of product). Mix thoroughly.
7) Mix pools for a minimum of 2 hours prior to measuring sedimentation rates.

Testing is then conducted with Modified Westergren and Mini Ves methodologies. Testing consists of five replicates/day for three days. The controls function to replicate the erythrocyte sedimentation rate characteristics of human whole blood.

The controls exhibit the following concentrations:

| COMPONENT/PARAMETER | LEVEL #1 | LEVEL #2 |
|---|---|---|
| RBC COUNT (x $10^{12}$/L) | $2.25 \times 10^{12}/L \pm .05 \times 10^{12}/L$. | $1.30 \times 10^{12}/L \pm .05 \times 10^{12}/L$. |
| COLLOID BP (2.5% STOCK IN PBS) | 50 MG % (20 ML/L) | 25 MG % (10 ML/L) |
| TRITON X-705 (10% STOCK IN PBS) | 50 MG % (5 ML/L) | 25 MG % (2.5 ML/L) |

EXAMPLE 2

1) Fix and stabilize human RBC with 0.08% glutaraldehyde, with the glutaraldehyde calculation being based on volume, RBC count ($4.0\times10^{12}/l\pm0.25\times10^{12}/l$) and target glutaraldehyde concentration.
2) Remove the glutaraldehyde by washing glutaraldehyde treated RBC three times with an equal volume of PBS. Adjust the RBC count to $4.0\times10^{12}/l\pm0.25\times10^{12}/l$ after completion of the washing segment.
3) Gravity settle the RBCs and remove the resulting supernatant. Resuspend the RBC with a solution of 40% 2-Propanol in PBS (v/v), and to a count of $1.0\times10^{12}/l\pm0.15\times10^{12}/l$. Gravity settle the alcohol treated RBCs overnight.
4) Remove alcohol solution and resuspend the RBCs in PBS. Wash RBCs 3 times with an equal volume of PBS. Following completion of the washing segment, adjust the RBC counts according to the level specific specifications. The RBC specification for level #1 is set at $2.25\times10^{12}/l\pm0.05\times10^{12}/l$. The RBC specification for level #2 is set at $1.3\times10^{12}/l\pm0.05\times10^{12}/l$
5) Add Lupasol P (1.0% stock solution in PBS) to the RBC pool volumes according to the level specific specifications so that final Lupasol P concentration for level #1 is at 5 mg % (5 ml of Lupasol P stock/liter of product) and 2.5 mg % for level #2 (2.5 ml of Lupasol P stock/liter of product). Mix thoroughly.
6) Add Triton X-705 (10% stock solution in PBS) to the RBC pool volumes according to the level specific specifications, so that final Triton x-705 concentration for level #1 is @ 50 mg % (5.0 ml of Triton X-705 stock/liter of product) and 25 mg % for level #2 (2.5 ml of Triton X-705 stock/liter of product). Mix thoroughly.
7) Mix pools for a minimum of 2 hours prior to measuring sedimentation rates.

Testing is then conducted with Modified Westergren and Mini Ves methodologies. Testing consists of five replicates/day for three days. The controls function to replicate the erythrocyte sedimentation rate characteristics of human whole blood.

The controls exhibit the following concentrations:

| COMPONENT CONC. | LEVEL #1 | LEVEL #2 |
|---|---|---|
| RBC COUNT ($\times 10^{12}/L$) | $2.25 \times 10^{12}/L \pm .05 \times 10^{12}/L$ | $1.30 \times 10^{12}/L \pm .05 \times 10^{12}/L$ |
| LUPASOL P (1.0% STOCK IN PBS) | 5 MG % | 2.5 MG % |
| TRITON X-705 (10% STOCK IN PBS) | 50 MG % | 25 MG % |

Although the invention has been described with particular reference to certain preferred embodiments thereof, variations and modifications can be effected within the spirit and scope of the following claims.

What is claimed is:

1. A control for use in an indirect acute phase protein measurement test, comprising:
   a) a plurality of substantially uniformly shaped cells;
   b) a surfactant; and
   c) an aggregating agent,
      wherein said aggregating agent and said surfactant are different chemical substances.

2. The control of claim 1, wherein said cells are comprised of red blood cell surrogates.

3. The control of claim 1, wherein said cells are comprised of human red blood cells.

4. The control of claim 1, wherein said surfactant includes an alkylene oxide functional group.

5. The control of claim 1, wherein said cells are comprised of porcine cells.

6. The control of claim 1, wherein said cells are comprised of bovine cells.

7. The control of claim 1, wherein said aggregating agent is selected from the group consisting of minerals, cationic materials and mixtures thereof.

8. The control of claim 1, wherein said aggregating agent is selected from the group consisting of diatomaceous earth, bentonite, polyethyleneimine and mixtures thereof.

9. The control of claim 1, wherein said control exhibits a stable red coloring for at least 90 days.

10. The control of claim 1, wherein said stabilized cells have an average diameter of between about one half to about two-thirds of the normal diameter of like live cells.

11. A method for making a control for an indirect acute phase protein measurement test, comprising the steps of:
   a) providing a source of cells;
   b) isolating cells from said source;
   c) fixing the morphology of said cells to produce a plurality of substantially uniformly shaped cells;
   d) treating the cells with an alcohol for achieving long term color stability and to increase their density relative to untreated cells, and
   e) suspending the cells in a solution containing an aggregating agent and a surfactant, with said aggregating agent and said surfactant being different chemical substances.

12. The method of claim 11, wherein said cells are comprised of red blood cells.

13. The method of claim 11, wherein said cells are comprised of red blood cell surrogates.

14. The method of claim 11, wherein said treating step (d) includes contacting said cells with an aliphatic alcohol.

15. The method of claim 11, wherein said step of fixing the morphology of said cells is comprised of fixing said cells with a glutaraldehyde.

16. The method of claim 15, wherein said surfactant includes an alkylene oxide group.

17. The method of claim 16 wherein said surfactant includes an ethylene oxide group.

18. The method of claim 11, wherein said aggregating agent is selected from the group consisting of minerals, polycationic materials and mixtures thereof.

19. The method of claim 11, wherein said aggregating agent is selected from the group consisting of diatomaceous earth, bentonite, polyethyleneimine and mixtures thereof.

20. A method for measuring an erythrocyte sedimentation rate, comprising the steps of:
   a) providing an erythrocyte sedimentation rate test instrument;
   b) providing a control for use in said test instrument; said control having
      i) a plurality of substantially uniformly shaped cells;
      ii) a surfactant; and
      iii) a finely divided solid aggregating agent with said aggregating agent and said surfactant being different chemical substances;
   c) testing a blood specimen in said instrument;
   d) testing said control in said instrument; and
   e) comparing the results of said blood specimen test of step (c) with the results of said control test of step (d).

21. The method of claim 20, wherein said instrument is an automated instrument.

22. The method of claim 20, wherein said instrument is a manual instrument.

23. A control for use in an indirect acute phase protein measurement test, comprising:
   a) a plurality of substantially uniformly shaped cells comprised of red blood cell surrogates;
   b) a surfactant including an alkylene oxide functional group; and
   c) an aggregating agent selected from the group consisting of diatomaceous earth, bentonite, polyethyleneimine and mixtures thereof.

24. The control of claim 23 wherein said red blood cell surrogates are derived from human, bovine or porcine blood.

25. The control of claim 23, wherein the control retains color stability for at least 90 days at about 50° C., at least about 6 months at about 22° C. or both.

26. The control of claim 23, wherein the aggregating agent is diatomaceous earth.

27. The control of claim 23, wherein the aggregating agent is bentonite.

28. The control of claim 23, wherein the aggregating agent is polyethyleneimine.

* * * * *

UNITED STATES PATENT AND TRADEMARK OFFICE
CERTIFICATE OF CORRECTION

PATENT NO. : 6,531,321 B1
DATED : March 11, 2003
INVENTOR(S) : Wayne L. Ryan et al.

It is certified that error appears in the above-identified patent and that said Letters Patent is hereby corrected as shown below:

<u>Title page,</u>
Item [75], after the word "Hunsley" delete "LaVista" and insert -- Omaha --
Item [56], References Cited, U.S. PATENT DOCUMENTS, delete "2,727,383" and insert -- 2,727,838 --

Signed and Sealed this

Twelfth Day of August, 2003

JAMES E. ROGAN
*Director of the United States Patent and Trademark Office*